(12) United States Patent
Zeng

(10) Patent No.: US 7,862,838 B1
(45) Date of Patent: Jan. 4, 2011

(54) COMPOSITION AND REGIMEN FOR THE TREATMENT OF HERPES SIMPLEX AND HERPES ZOSTER PRIMARILY BY ELIMINATING THEIR PATHOGENETIC CONDITIONS AND TAKING INTO ACCOUNT BOTH PATHOGENESIS AND ETIOLOGY

(76) Inventor: Qing Si Zeng, 1436 Milton Ave., Alhambra, CA (US) 91803

( * ) Notice: Subject to any disclaimer, the term of this patent is extended or adjusted under 35 U.S.C. 154(b) by 0 days.

(21) Appl. No.: 12/584,042

(22) Filed: Aug. 31, 2009

(51) Int. Cl.
*A61K 36/195* (2006.01)
*A61K 31/455* (2006.01)
*A61K 31/4375* (2006.01)

(52) U.S. Cl. .................. 424/725; 424/776; 514/52; 514/251; 514/276; 514/356; 562/562

(58) Field of Classification Search ................ None
See application file for complete search history.

(56) References Cited

U.S. PATENT DOCUMENTS

2005/0256031 A1* 11/2005 Hageman et al. ............... 514/2

OTHER PUBLICATIONS

Tanaka (Chem. Pharm. Bull. (2004), vol. 52, No. 10, pp. 1242-1245).*

* cited by examiner

*Primary Examiner*—Susan C Hoffman

(57) ABSTRACT

A composition and regimen for the treatment of herpes simplex and herpes zoster, primarily through elimination of the pathogenetic conditions by taking into account both pathogenesis and etiology thereof are disclosed. Administration of 1) repeated large dosages of vitamin B2 to eliminate severe vitamin B2 deficiency inherent in herpes simplex and herpes zoster; 2) Strobilanthes cusia and Berberine to ameliorate febrile illness and to clear "hot" condition; 3) Zizyphus semen to relieve psychological stress; and 4) L-lysine to antagonize arginine and alleviate anxiety-all these hereof are for eliminating the pathogenetic conditions. These, in combination with antiviral agents if necessary, constitute the scope and the spirit of the present invention.

12 Claims, No Drawings

COMPOSITION AND REGIMEN FOR THE TREATMENT OF HERPES SIMPLEX AND HERPES ZOSTER PRIMARILY BY ELIMINATING THEIR PATHOGENETIC CONDITIONS AND TAKING INTO ACCOUNT BOTH PATHOGENESIS AND ETIOLOGY

BACKGROUND OF THE INVENTION

1. Field of the Invention

The present invention relates to a composition and regimen for the treatment of herpes simplex (herpes labialis and herpes genitalis) and herpes zoster, primarily by means of eliminating their pathogenetic conditions, taking into account both pathogenesis and etiology thereof.

2. Background of the Related Art

As of today, antiviral agents such as acyclovir are used primarily for the treatment of herpes simplex (herpes labialis or herpes genitalis) and herpes zoster. These antiviral agents are somewhat effective but not satisfactory.

Antiviral treatment is an etiological treatment. However, an etiologic agent may cause a disease only under certain pathogenetic conditions, like a seed that needs soil and moisture to germinate.

The conditions for the pathogenesis of herpes simplex and herpes zoster involve several aspects, and will be stated in the subsequent description of the present invention.

Treatment by lysine supplement has been reported frequently with conflicting results.

Heretofore, no report has been found to pay due attention to and deal with the pathogenetic conditions underlying herpes simplex and herpes zoster.

Without eliminating the pathogenetic conditions thereof, any antiviral agent's efficacy is limited.

Therefore, it is necessary to provide a composition and regimen which, by mainly eliminating the pathogenetic conditions thereof and considering the etiology, makes the treatment of herpes simplex and herpes zoster more reasonable and effective, and with less time and side-effects.

BRIEF SUMMARY OF THE INVENTION

The present invention is to achieve the foregoing object, i.e., to provide a composition and regimen for the treatment of herpes simplex and herpes zoster by means of eliminating the pathogenetic conditions, and taking into account both pathogenesis and etiology thereof.

The conditions for the pathogenesis of herpes simplex and herpes zoster, as investigated by the present applicant, involve at least the following:

1) Severe vitamin $B_2$ deficiency or ariboflavinosis
2) Febrile illness, or "hot" condition, either systemic or local
3) Physical or psychological stress
4) High arginine intake and/or low lysine intake Some of the conditions cited above are well known, but treatments of herpes simplex or herpes zoster by means of eliminating these conditions are rarely reported.

A composition and regimen of the present invention for eliminating the pathogenetic conditions of herpes simplex and herpes zoster are provided herein.

The composition of the present invention comprises a daily dosage of:

a) Vitamin $B_2$, from about 20 to 200 mg
b) Vitamin $B_{co}$: $B_1$ from about 1.5 to 3 mg, $B_2$ from about 1.7 to 3.5 mg, $B_6$ from about 2 to 4 mg, $B_{12}$ from about 6 to 12 mcg, biotin from about 30 to 60 mcg, niacin from about 20 to 40 mg, folic acid from about 400 to 800 mcg, panthothenic acid from about 10 to 20 mg
c) (1:5) concentrated Strobilanthes cusia (Qingdai), from about 200 to 600 mg; or Isatis tinctoria radix (Banlangen), from about 2 to 10 g, or Isatis tinctoria folium (Daqingye), from about 2 to 10 g
d) Berberine, from about 600 to 1200 mg
e) (1:5) concentrated Zizyphus semen, from about 2 to 6 g
f) L-lysine, from about 1 to 2 g The daily dosage hereof is divided into from about 4 to 10 doses and each dose is administered at an appropriate interval of time.

The daily dosage hereof is adjusted by age, body weigh, and by particular conditions as severity, systemic symptoms, complications and so on. In severe cases, the dosage may be adjusted by the prescribing health care provider.

For the sake of convenience, the composition of the present invention can be compounded into a capsule or a tablet form, by adding suitable inactive ingredients well known in the art. Each capsule or tablet hereof contains the components of said composition as in the following formula:

a) Vitamin $B_2$ 10 mg
b) Vitamin $B_{co}$: $B_1$ 0.3 mg, $B_2$ 0.4 mg, $B_6$ 0.4 mg, $B_{12}$ 1.2 mcg, biotin 6 60 mcg, niacin 4 mg, folic acid 80 mcg, panthothenic acid 2 mg (Doses may vary)
c) (1:5) concentrated Strobilanthes cusia (Qingdai) 40 mg
d) Berberine 100 mg
e) (1:5) concentrated Zizyphus semen 200 mg
f) L-lysine 150 mg The composition of the present invention may also be compounded into an injection or an ointment or a cream form, by means of adding inactive ingredients well known in the art.

The treatment regimen of the present invention comprises: Initially, administering to the patient 2 capsules (or tablets, the same hereinafter) of said formula orally every 2-4 hours. The dosage may be higher in severe cases, and may be adjusted by the prescribing health care provider. When symptoms are alleviated (see description below), usually after 1-2 days, administer 1 capsule of said formula every 4 hours until symptoms disappear.

Injection of the composition can be applied independently or combined with oral administration. Ointment or cream is intended for cutaneous use only and should not be used in the eye or on mucous membrane.

Oral administration alone of said formula following the regimen described above is effective for most cases. However, it is advisable to combine with antiviral agents such as acyclovir in severe cases, as directed by the prescribing physician.

For most cases, the local symptoms of a stinging and burning sensation and pain begin to relieve quickly in about 2 hours after the first administration of said formula, with lesions of blisters or ulcers ceasing to progress, fever and systemic symptoms ameliorating gradually, and the color of urine changing from light yellow to dark yellow.

After about 2-4 hours, pain and a stinging, burning sensation will re-appear, and the color of urine will return to light yellow again. Therefore repeated administration of said formula is mandatory until the symptoms completely disappear.

Both the relapse of local symptoms and the color of urine returning to light yellow serve as indicators for repeated administration of said formula. Tests of riboflavin concentration in urine and/or FAD, FMN level in blood provide additional guidance.

The average total period of treatment with the present invention is from about 2-4 days for herpes simplex and from about 3-7 days for herpes zoster. After the acute stage, crusts of the lesion form and fall off gradually, and then a red spot or spots remain for some more days.

For better results of the treatment with the present invention:
1. Avoid overexposure of sunlight
2. Avoid spicy or fried, toasted, grilled food
3. Consume less peanuts or nuts
4. Do not apply glucocorticoids except in case of adrenal insufficiency
5. Do not administer large dose of vitamin C
6. Avoid alcohol and tobacco The formula of the present invention can be used for therapeutic prevention of herpes simplex: Whenever the patient feels a stinging and burning sensation on the potential site, or feels roughness on the tip of the tongue, he can ingest 1-2 capsules of the formula, and repeat every 2-4 hours if necessary. The measure thereof will mostly abort an episode of herpes simplex. After several such preventive measures, recurrence of herpes simplex will be less and less likely, or latent for a sustained period.

The formula of the present invention can also be used for routine prevention of herpes simplex: Taking 1 capsule once or twice a week may prevent herpes simplex from recurrence for a sustained period.

Herpes zoster rarely recurs.

As varicella (commonly known as "chicken pox") shares the same etiologic virus (VZV) with herpes zoster, it is reasonable to apply the present invention for the treatment of varicella.

The present invention is also effective for some cases of Bell's palsy at their early stages.

The composition of the present invention has little side-effects at the recommended dosage and regimen described above. Occasionally some patients may complain of discomfort in the stomach, mild diarrhea, palpitation, or low blood pressure, usually due to overdose. Reducing dosage thereby is recommended. The composition of the present invention is contraindicated in patients with known hypersensitivity to any component of said composition.

DETAILED DESCRIPTION OF THE INVENTION

1) The special feature of the present invention is to treat herpes simplex and herpes zoster primarily by means of eliminating the underlying pathogenetic conditions, taking into account of both pathogenesis and etiology thereof.

As of today, antivirus agents are used primarily for the treatment of herpes simplex and herpes zoster. Just like antibiotics for the treatment of bacterial infection, this is an etiological therapy. However, for the development of herpes simplex and herpes zoster, there exist special conditions of pathogenesis as described above. Without eliminating these conditions, antiviral agents alone are much less effective.

2) In the present invention the applicant indicates that, among the pathogenetic conditions of herpes simplex and herpes zoster set forth above, severe vitamin $B_2$ deficiency or ariboflavinosis is the most important one. The applicant found this fact many years ago, and sent a letter to the editor of Lancet in November, 1996 (see the copy enclosed), indicating the ariboflavinosis condition in herpes simplex, and the approach by repeated large doses of vitamin $B_2$ (together with Chinese herbs and/or antiviral agents) to treat herpes simplex and herpes zoster.

The first importance of the present invention is "to repeat administration of large dose of vitamin $B_2$", because patients with herpes simplex and herpes zoster have severe (not ordinary) vitamin $B_2$ deficiency or ariboflavinosis.

The symptoms and signs of ordinary vitamin $B_2$ deficiency are: angular stomatitis, cheilosis, glossitis, red, scaly, greasy skin on face, eyelids, scrotum or labia majora.

Herpes simplex and herpes zoster are infectious diseases caused by a virus. Herpes simplex and herpes zoster have relation with vitamin $B_2$ deficiency, but they are not the same identity. Severe vitamin $B_2$ deficiency or ariboflavinosis is one of the underlying conditions for the pathogenesis of herpes simplex or herpes zoster.

The fact that patients with herpes simplex or herpes zoster having severe vitamin $B_2$ deficiency can be understood by the following manifestation: a healthy person will have dark yellow or orange color of urine after ingesting 2 mg of vitamin $B_2$ (hereafter abbreviated as $B_2$) because unused, extra $B_2$ is excreted from the body. However, patients with herpes simplex or herpes zoster will have only a slight yellow color of urine even after ingesting 10 times that amount, i.e., 20 mg of $B_2$. As $B_2$ can be stored in only trace amounts in the body, the light yellow color of urine implies that a large amount of $B_2$ has been consumed. A test of $B_2$ concentration in the urine or FAD, FMN levels in the blood may confirm the fact hereof.

Following repeated administration of vitamin $B_2$, together with the color change of urine, local stinging discomfort and burning sensation relieve quickly, topical lesions of blisters or ulcers cease to progress, fever or systemic symptoms, if any, ameliorate, and will disappear in a few days.

If a patient with herpes simplex or herpes zoster has high fever, or systemic symptoms like irritation, nervousness, sleeplessness, viremia, as well as complications of the nervous system, the patient will not be relieved effectively if only antiviral agents or lysine are applied without the pathogenetic conditions being eliminated.

Why should the condition of severe vitamin $B_2$ deficiency exist in patients with herpes simplex and herpes zoster?

Although severe vitamin $B_2$ deficiency may be due to chronic malnutrition, more likely it is because of acute depletion of $B_2$.

Systemic or local febrile illness, any "hot" condition without obvious infection, overexposure to sunlight, over consumption of spicy, grilled food, or physical or psychological stress, will increase metabolism in general and especially in herpes virus preferred sites. As FAD and FMN participate in comprehensive aspects of cell metabolism, inevitably they will be consumed and depleted. Vitamin $B_2$ is the essential part of FAD and FMN, so will be consumed and depleted as well.

Some might speculate: severe vitamin $B_2$ deficiency is due to $B_2$ being consumed by virus replication. If so, then a supplement of $B_2$ would benefit virus replication and make symptom worse, but this is not the case.

Why should administration of $B_2$ be effective to block the progress of herpes simplex or herpes zoster?

Severe Vitamin $B_2$ deficiency and FAD, FMN depletion hinder the normal metabolism of the host cells by, for example, impairing the function of mitochondria, enhancing oxidation, releasing free radicles and NO, etc. [1 Wacker et al., 2000], resulting in functional impairment and structural damage of the host cells, hence herpes virus invasion or dormant virus becoming active. Administration of $B_2$ recovers the host cell's ability to resist virus invasion.

In summary a hypothesis is hereby disclosed: Increasing metabolism in general and especially in certain parts of the body, either by febrile illness or other conditions→depletion of FAD, FMN and vitamin $B_2$→impairment of metabolism of the cells→functional and structural damage of the cells→herpes virus invasion on the preferred sites→development of herpes simplex and herpes zoster.

However, repeated administration of large dosage of vitamin $B_2 \rightarrow$ host cells recover from damage→herpes simplex or herpes zoster heals.

In addition to large dosage of $B_2$, co-administration of vitamin $B_{co}$ at 1-2-fold dosage of recommended daily value will be beneficial, because there may also be vitamin $B_{co}$ deficiency co-existing with $B_2$ deficiency. However, any component other than $B_2$ in vitamin $B_{co}$, including vitamin $B_6$, niacin, folic acid etc. can not replace the role of vitamin $B_2$.

3) On the pathogenetic conditions described above, patients with herpes simplex and herpes zoster always present febrile illnesses, such as common cold, flu, upper respiratory infection, or local inflammation in the mouth, on the face or on the genital organ.

During infection bacteria produce endotoxin lipopolysaccharide (LPS), which stimulate macrophages and lymphocytes to release cytokines such as IL-1, IL-6, TNF-α, INF-γ, HMGB1, and pro-inflammatory mediators COX-2, NO, etc. These factors in turn induce inflammation. In addition, there are also increased sympathetic-adrenal activity and enhanced hypothalamic-pituitary-adrenal cortical (HPA) response. All these will result in increasing metabolism, and leading to FAD, FMN and vitamin $B_2$ depletion.

In some cases there may be no obvious inflammation, but there may be dryness of the mouth and the tongue, excessive thirst, flush, restlessness or difficulty in sleep, urine less in volume and more yellow in color, as well as dry and hard stool, etc. This may be called "hot" condition, and "hot" condition implies increased metabolism.

Clinical experience revealed that if a person has no febrile illnesses or "hot" condition, and he always feels much moisture in the mouth, has plenty of clear urine, soft stool, or even feels cold in his hands and feet, he would rarely develop herpes simplex or herpes zoster.

On the pathogenetic conditions described herein above, overexposure to sunlight, or spicy seasoning or its ingredient capsaicin [[2] Watanabe et al., 1991; [3]Lim et al., 1997], or consumption of fried, grilled food may stimulate metabolism and deplete vitamin $B_2$, predisposing the body to invasion of herpes simplex or herpes zoster.

4) The effects of medicinal herbs a) Strobilanthes cusia (Qingdai) or Isatis tinctoria radix (Banlangen) or Isatis tinctoria folium (Daqingye) have similar effects in "heat-clearing" but their efficiency may vary.

The concentrated forms or extracts thereof are used in clinical practice of Chinese medicine and for research. Some of the ingredients thereof have been purified. As "heat-clearing" herbs in Chinese medicine they are used to treat flu, respiratory infection, pneumonia, meningitis, skin infection, and herpes virus disease, mump, hepatitis, etc.

These herbs have been found in vitro to a certain extent inhibit several types of bacteria [[4]Bansky et al., 1993; [5]Xiao et al., 2003] and virus [[6]Tanaka et al., 2004; [7]Li et al., 1994]. However, their "heat-clearing" or anti-inflammatory effects are not only due to inhibition against bacteria or virus, but also due to other mechanism.

In animal experiments they manifest significant effect against chemically induced inflammation [[8]Ho et al., 2003; [9]Ho et al., 2002; [10]Recio et al., 2006]. They destroy or inactivate endotoxin LPS [[11]Liu et al., 1994]; inhibit the production and release of inflammatory mediators [[12]Wu et al., 2001; [13]Molina et al., 2001; [14]Danz et al., 2001]. They may also inhibit inflammation through modulating the immune system [[15]Kunikata et al., 2000; [7]Li et al., 1994].

Strobilanthes cusia (Qingdai) or its relatives are selected for the composition of the present invention because they demonstrate beneficial results in patients of herpes simplex or herpes zoster especially with general inflammation like flu, respiratory infection, fever, etc.

b) Berberine is extracted from Coptis chinese, Coptis deltoidea, Coptis teeta, Hydrastis canadenses, or Berberis vulgaris, berberis aquifolium, berberis aristata, etc., or synthesized.

Berberine is used in Chinese medicine as a "heat-clearing, damp-drying" agent to treat intestinal infection, gingivitis, sore throat, conjunctivitis, eczema, etc.

Berberine manifests in vitro to a certain extent inhibitory effects against many types of virus, chlamydia, bacteria, fungi, parasites [[16]Birdsal et al., 1997; [17]Li et al., 2002].

However, berberine possesses anti-inflammatory effect not only by inhibiting pathogen, but also by other actions. Berberine inhibits chemical inflammatory reaction in experimental animals, also inhibits delayed supersensitive activity [[18]Ivanovska et al., 1996; [19]Esra et al., 2002]. Berberine destroys endotoxin [[20]Jiang et al., 2002]; inhibits the release of inflammatory mediators [[21]Kuo et al., 2004; [22]Lee et al., 2003]. Berberine as an antagonist for cholesterase enhances the activity of acetylcholine [[23]Kuznetsova et al., 2002], resulting in inhibition of inflammation [[24]Borovikova 2000].

During the past decades, berberine has been found to be efficacious in many other aspects such as reducing blood glucose [[25]Wang et al., 2003], decreasing blood lipids [[26]Kong et al., 2005], and lowering blood pressure [[27]Ko et al., 1980]. Berberine has also been reported to have good results in the treatment of congestive heart failure [[28]Zeng et al., 2003; [29]Kang et al., 2002; 30 Marin-Neto et al., 1998].

Berberine is especially useful in patients of herpes simplex or herpes zoster with local inflammation in or around the mouth like gingivitis, pharyngitis, or sores on the face or genital organ.

Strobilanthes cusia or its relatives, together with berberine, selected in the present composition, are supposed to clear febrile illness or "hot" condition set forth in item 2 above of pathogenetic conditions. Therefore, the application of any "heat-clearing" herbs, including but not limited to *Peonea cortex, Lithospermum radix, Forththia fructus, Gentiana radix, Scutellaria radix, Artemisia annua, Neopicrorhiza rhizome*, or the application of antibiotics to control infection, which will lead to decreased hypermetabolism and reduce the depletion of FAD, FMN and vitamin $B_2$, finally result in the amelioration of herpes simplex or herpes zoster, should be understood as within the scope and the spirit of the present claimed invention.

5) Psychological stress such as anger, anxiety, depression, and physical stress such as injury, surgery, and dental procedure are always predisposed to herpes simplex and herpes zoster. Just as inflammation, stress stimulates sympathetic adrenal activity and HPA response, and leads to increased metabolism. All these will result in depletion of FAD, FMN and vitamin $B_2$.

Herbs like Zizyphus semen with its calming and sedative action, is effective for the relief of anxiety and insomnia [[31]Chen et al., 2002; [32]Yuan et al., 1987], so is good for the amelioration of Herpes simplex or herpes zoster.

Herbs like Zizyphus semen, including but not limited to Biota semen, Polygala tenuifolia radix, Polygonum multiforum, or stress relief medicine such as melatonin or Valium, have similar effects in relieving stress and thus can lead to decreased $B_2$ depletion, are beneficial to the amelioration of Herpes simplex or herpes zoster. Therefore, they should be understood as within the scope and the spirit of the present claimed invention.

6) L-lysine is good for patients with herpes simplex or herpes zoster who have consumed large amounts of peanuts or nuts, or have encountered psychological stress.

The mechanism through which lysine works comprises:

a) peanuts and nuts are rich in arginine, an amino acid which is an important ingredient of the core protein of virion, and is essential for virus replication [[33]Becker et al., 1967], whereas lysine as an anti-metabolite of arginine, may block arginine's role in viral replication; low ratio of lysine/arginine in food enhances viral replication and vice versa [[34]Griffith et al., 1981].

b) Lysine deficiency induces anxiety [[35]Smriga et al., 2002]; lysine supplement decreases stress-induced sympathetic adrenal activity and HPA response, resulting in relief of anxiety [[36]Smriga et al., 2004].

Many reports stated that lysine was not always effective in ameliorating herpes simplex. Considering that low lysine is but one of the pathogenetic conditions described above, one may easily understand the reason.

7) Glucocorticoid steroid: As in chickenpox, steroid is contraindicated in herpes simplex and herpes zoster because of its immunosuppressive action. The present applicant's experience indicated that for patients taking steroids previously, the application of the present invention is always less effective. Therefore, the applicant's suggestion is: in case of no obvious indication of adrenal insufficiency, no steroid is necessary; even if it is indicated in case of adrenal insufficiency, appropriate supplement of Glucocorticoid (but not in large dosage) may be good.

8) Vitamin C: According to the applicant's experience, large dosage (200-500 mg) of vitamin C made herpes simplex worse. This may be due to the involvement of vitamin C in glucocorticoid synthesis: it's well known that abundant vitamin C is stored in the adrenal gland; and vitamin C participates in the synthesis of steroid hormones [[37]Bjorkhem et al., 1978].

Therefore, large dosage of vitamin C is also not recommended for the treatment of herpes simples and herpes zoster.

9) The composition and the regimen of the present invention are primarily elimination of the pathogenetic conditions of herpes simplex and herpes zoster. In most cases, the composition and the regimen of the present invention alone is enough to heal herpes simplex or herpes zoster. The present invention is effective, quick, economical, and has little side-effect. However, the statement hereof dose not mean excluding the co-administration of antiviral agents such as acyclovir. As a matter of fact, the integration of anti-etiologic therapy with anti-pathogenetic therapy should be a more reasonable and ideal strategy.

10) As varicella share the same etiologic virus (VZV) with herpes zoster, it is reasonable to apply the present invention for the treatment of varicella.

11) The present invention is also effective for some cases of Bell's palsy at their early stages.

12) Following the regimen of the present invention as set forth above, it has been found that the composition hereof has little adverse reactions. In case someone complains of discomfort in the stomach after administration, reducing the dosage is recommended, or cease administration if necessary. The composition of the present invention is contraindicated in patients with known hypersensitivity to any component hereof.

EXAMPLES

1) D.C.M, male, 35, engineer

Patient complained of painful blisters on the corner of the lips for two days.

Patient stated that he had had recurrent maceration in the angles of the mouth since childhood. Sometimes the lesion became worse, and formed a cluster of small blisters, followed by ulcer formation, having painful impact on eating, sleeping, and working. Most frequently it occurred under pressure of work or after insomnia.

After examination, the patient was given 24 capsules of the formula, and was instructed to follow the regimen as set forth in the patent application above. When following up with the patient by phone the next day, he answered that the pain had eased quickly, and the lesion was getting dry. On the third day the crust fell little by little and cleared by the fifth day, and there remained a red spot for some more days.

2) A.F.C., male, 71, retired physician

Patient reported that he had suffered from recurrent herpes simplex around the lips or inside the mouth since childhood, it usually occurred after pressure of work or mild febrile illness, 5-7 episodes per year. He prescribed acyclovir and vitamin $B_{co}$ for himself and the lesion would heal gradually in two weeks.

He consulted the patent applicant four years ago. The patent applicant referred him to the composition and regimen of the present invention, plus acyclovir. He was pleased with the quick effectiveness of the treatment: pain eased in two hours, blisters dried gradually in two days, and the crust fell in 3-4 days.

He practiced the preventive therapy: Whenever he anticipated an episode by feeling stinging and burning in the potential site, or roughness on the tip of the tongue, he ingested one capsule of the formula immediately and repeated once after 2-3 hours. Usually this measure would prevent herpes simplex from outbreak. Even if it occurred, it would be mild and easier to treat.

He again started routine prevention by taking one capsule once a week, and has had no episode for more than two years.

The doctor encouraged the patent applicant to apply for a patent and to have it on the market so as to benefit more patients.

3) S.M.B., female, 28, horse trainer

Patient had genital herpes for three days, and was referred to this office by her family doctor.

She reported having recurrence of genital herpes for a couple of years, more frequently during the summer, about 1-2 episodes a month. She noticed the recurrence was related to over exposure to sunlight.

She was giving 20 capsules of the present formula. After three days, she came back to the office relating that her pain was alleviated quickly in 2 hours, and now the lesion was almost gone. She came back requesting to have more capsules for prevention.

4) M.L., female baby, 11 months (as reported by the baby's mother) Baby had had fever for four days. She was diagnosed with flu and was administered antibiotics and antipyretics by a local clinic. Fever was relieved for only a few hours after each administration. Baby appeared restless two days ago and then became lethargic.

Rectal temperature was 40° C. Several white ulcers on the surface of the tongue and the mucous membrane of the mouth were found by oral examination.

One half capsule of the formula was dissolved in water and fed to the baby. 5% glucose in saline was infused through frontal vein. Cold packs were placed on the forehead, axillae and the groins to help lower temperature. Fever decreased gradually after about three hours. The same dose of the formula was repeated every 3-4 hours. On the third day the temperature decreased to 37° C. Baby began to cry and suck milk little by little. On the fourth day her fever was gone. Her mother was instructed to administer ¼ capsule of the formula four times daily for two more days. The baby recovered completely.

C.G.L., male, 48, teacher

Patient reported suffering severe pain around his right eye for four days, and was diagnosed with herpes zoster by a clinic two days ago. He had been taking acyclovir and got some relief, though still endured pain especially at night. Ibuprofen was effective only for a short time.

For quicker relief, the patient preferred to take the formula of the present invention along with acyclovir. Pain eased quickly and was almost gone in two days. Patient was advised to keep treatment with one capsule four times daily for five more days, and was subsequently healed.

REFERENCES

The following references are specially incorporated herein by reference in pertinent part for the purposes indicated.
1. Wacker J, et al: Riboflavin deficiency and preeclampsia. Obstet. Gynecol. 2000, 96(1):38-44.
2. Watanabe A, Kawata T, et al: Thermogenic action of capsaicin and its analogs. In Obesity: Dietary factors and Control. (Suzuki M, editor). 1991, pp 67-77. Japan Scientific Society Press, Tokyo.
3. Lim K, et al: Dietary red pepper ingestion increases carbohydrate oxidation at rest and during exercise in runners. Medicine & Science in Sports & Exercise. 1997, 29(3): 355-61.
4. Bansky D, Gamble A: Chinese Herbal Medicine, Materia Medica. Rev. ed. 1993, Eastland Press, Seattle.
5. Xiao S S, et al: Banlangen (Isatis tinctoria): Its ingredients, pharmacology and quality control. J Shenyang Pharmaceut Univ, 2003; 20 (6):455-9. (In Chinese).
6. Tanaka T, Ikeda T, Kaku M, Zhu X H, et al: A new lignan glucoside and phenylethanoid glucosides cusia. Chemical and Pharmaceutical bulletin 2004, vol. 52, n. 10, pp. 1242-45.
7. Li L, Dong T Y et al: Quality control of Isatis tinctoria (leaf) and its preparations. Acta Pharmaceut Sinica, 1944, 29 (2):128-310 (In Chinese).
8. Ho Y L, Kao K C, et al: Evaluation of antinociceptive, anti-inflammatory and antipyretic effects of Strobilanthes cusia leaf extract in male mice and rats. Am J Chin Med. 2003; 31(1):61-9.
9. Ho Y L, Chang Y S: Studies on the antinociceptive, anti-inflammatory and anti pyretic effects of Isatis indigotica root. Phytomedicine. 2002; 9(5):419-24.
10. Recio M C, Cerda-Nicolas M, et al: Anti-inflammatory and antiallergic activity in vivo of lipophilic Isatis tinctoria extracts and trptanthrin. Planta Med 2006; 72(6):539-46.
11. Liu Y H, Liu Y B: Banlangen: its antitoxin action and the comparison of their efficiency among different sources. China J Chinese Meteria Medica 1994, 19(2):88-90. (In Chinese).
12. Wu H P, Chen J X, et al: Influence of banlangen polysaccharide on binding activity of NFκB. Pham Biotechnol, 2001; 8(5):276-8.
13. Molina P, Tarraga A, et al: Inhibition of leukocyte functions by the alkaloid isaindigotone from Isatis indigotica and some new synthetic derivatives. J Nat. Prod. 2001; 64(10):1297-300.
14. Danz H, Stoyanova S, et al: Identification and isolation of the cyclooxigenase-2 inhibitory principle in Isatis tinctoria. Planta Med. 2001; 67(5):411-6.
15. Kunikata T, Tatefuji T, et al: Indirubin inhibits inflammatory reactions in delayed-type hypersensitivity. Eur J. Pharmacol. 2000; 410(1):93-100.
16. Birdsall T C, Kelly G S: Berberine: Therapeutic potential of an alkaloid found in several medicinal plants. Ahern Med Rev, 1997; 70:233-41.
17. Li Q R, Ren J K et al.: Anti-bacterial effects of 18 medicinal herbs. Shenxi Trad Chin Med, 2002; 23 (6): 555-6. (In Chinese).
18. Ivanovska N, Philipov S: Study on the anti-inflammatory action of Berberis ulgaris root extract, alkaloid fractions and pure alkaloids. Int J Immunopharmacol, 1996; 18(10): 553-61.
19. Esra Kupesi, et al: A comparative study on the anti-inflammatory, antinociceptive and antipyretic effects of isoquinoline alkaloids from the roots of Turkish Berberis species. Life Sci. 2002; 72(6):645-57.
20. Jiang Q C, Wang Y M et al: Investigation of in vivo anti-bacterial endotoxin effects of berberine compound injection. Chin J Hosp Pharmacy, 2002; 22 (5):276-8. (In Chinese).
21. Kuo C L, Chi C W, Liu T Y: The anti-inflammatory potential of berberine in vitro and in vivo. Cancer Lett 2004, 203(2):127-37.
22. Lee D U, Kang Y J: Effects of 13-alkyl-substituted berberine alkaloids on the expression of COX-II, TNF-α, iNOS, and IL-12 production in LPS-stimulated macrophages. Life Sci, 2003; 73(11):1401-12.
23. Kuznetsova L P, et al: Inhibition of human blood acetylcholinesterase and butyrylcholinesterase by some alkaloids. J Evolut Biochem Physiol. 2002; 38(1):35-9
24. Borovikova L, Ivanova S, et al: Role of vagus nerve signaling in CNI-1493 mediated suppression of acute inflammation. Autonomic neuroscience: basic & clinical. 2000, vol 95, n 12, pp 111-117.
25. Wang R, Gu Y R: Comparison of efficacy between berberine and DMBG on diabetes mellitus type II. Chin Arch Trad Chin Med, 2003; 21(7): 1189-90. (In Chinese).
26. Kong W, et al: Berberine is a novel cholesterol-lowering drug working through a unique mechanism distinct from statins. Nat Med 2005, 12:1344-51.
27. Ko S T, Lim D Y: Influence of berberine on the blood pressure of rabbits. Arch Pharmacol Res, 1980; 3(1):23-30.
28. Zeng X H, Zeng X J: Efficacy and safety of berberine for congestive heart failure secondary to ischemic or idiopathic dilated cardiomyopathy. Am J. Cardiol. 2003; 92(2): 173-6.
29. Kang Q Z, Ye F: Investigation on the treatment of 17 cases of congestive heart failure with berberine. Chin J Nat Med, 2002; 4 (2):83-4. (In Chinese).
30. Marin-Neto J A, et al: Cardiovascular effects of berberine in patients with severe congestive heart failure. Clin Cardiol, 1998; 11:253-60.
31. Chen B Q, et al: The sedative and hypnotic effects of saponin from zizyphus. J Chin Medicinal materials, 2002, 25(6):429-39.
32. Yuan C L, et al: The effective ingredients of flavonoids from zizyphus on sedative and hypnotic action. China J Chinese Meterica Medica, 1987, 12(9):34. (In Chinese).
33. Becker Y, Olshevsky U, Levitt J: The role of arginine in the replication of herpes simplex virus. Gen Virol, 1967, 1:471-8.

34. Griffith R S, DeLong D C, Nelson JD: Relation of arginine-lysine antagonism to herpes simplex growth in tissue culture. Chemotherapy. 1981, 27(3):209-13.
35. Smriga M, et al: Dietary L-lysine deficiency increases stress-induced anxiety and fecal excretion in rats. J. Nutr. 2002; 132:3744-6.
36. Smriga M, et al: Lysine fortification reduces anxiety and lessens stress in family members in economically weak communities in northwest Syria. Proc Natl Acad. Sci. 2004; 101(22):8285-8.
37. Bjorkhem I, Kallner A, Karlmar K E: Effects of ascorbic acid deficiency on adrenal mitochondrial hydroxylations in guinea pigs. J Lipid Res, 1978; 19 : 695-704.

I claim:

1. A composition for treating herpes simplex, herpes zoster or both comprising:
 a) about 20 to 200 mg Vitamin $B_2$;
 b) Vitamin $B_{co}$ which comprises about 1.5 to 3 mg Vitamin $B_1$, about 1.7 to 3.5 mg Vitamin $B_2$, about 2 to 4 mg Vitamin $B_6$, about 6 to 12 mcg Vitamin $B_{12}$, about 30 to 60 mcg biotin, about 20 to 40 mg niacin, about 400 to 800 mcg folic acid, and about 10 to 20 mg pantothenic acid;
 c) an ingredient selected from about 200 to 600 mg concentrated Strobilanthes cusia, about 2 to 10 g Isatis tinctoria radix, or about 2 to 10 g Isatis tinctoria folium;
 d) about 600 to 1200 mg Berberine;
 e) about 2 to 6 g concentrated Zizyphus semen; and
 f) about 1 to 2 g L-lysine.

2. The composition according to claim 1 further comprising an ingredient selected from Peony cortex, Lithospermum radix, Forsythia fructus, Gentiana radix, Scutellaria radix, Artemisia annua, Neopicrorhiza rhizome or antibiotics.

3. The composition according to claim 1 further comprising an ingredient selected from Biota semen, Polygala tenuifolia radix, Polygonum multiflorium, melatonin, or Valium.

4. The composition according to claim 1 further comprising inactive ingredients where the composition and the inactive ingredients are in the form of an injection, ointment, cream, capsule or tablet.

5. A capsule or tablet for treating herpes simplex, herpes zoster or both comprising:
 a) 10 mg Vitamin $B_2$;
 b) Vitamin $B_{co}$ which comprises 0.3 mg Vitamin $B_1$, 0.4 mg Vitamin $B_2$, 0.4 mg Vitamin $B_6$, 1.2 mcg Vitamin $B_{12}$, 60 mcg biotin, 4 mg niacin, 80 mcg folic acid, 2 mg pantothenic acid;
 c) 40 mg concentrated Strobilanthes cusia;
 d) 100 mg Berberine;
 e) 200 mg concentrated Zizyphus semen;
 f) 150 mg L-lysine.

6. A method for treating herpes simplex, herpes zoster, or both comprising administering to a patient in need thereof a composition comprising:
 a) about 20 to 200 mg Vitamin $B_2$;
 b) Vitamin $B_{co}$ which comprises about 1.5 to 3 mg Vitamin $B_1$, about 1.7 to 3.5 mg Vitamin $B_2$, about 2 to 4 mg Vitamin $B_6$, about 6 to 12 mcg Vitamin $B_{12}$, about 30 to 60 mcg biotin, about 20 to 40 mg niacin, about 400 to 800 mcg folic acid, and about 10 to 20 mg pantothenic acid;
 c) an ingredient selected from about 200 to 600 mg concentrated Strobilanthes cusia, about 2 to 10 g Isatis tinctoria radix, or about 2 to 10 g Isatis tinctoria folium;
 d) about 600 to 1200 mg Berberine;
 e) about 2 to 6 g concentrated Zizyphus semen; and
 f) about 1 to 2 g L-lysine.

7. The method according to claim 6 where the composition further comprises an ingredient selected from Peony cortex, Lithospermum radix, Forsythia fructus, Gentiana radix, Scutellaria radix, Artemisia annua, Neopicrorhiza rhizome or antibiotics.

8. The method according to claim 6 where the composition further comprises an ingredient selected from Biota semen, Polygala tenuifolia radix, Polygonum multiflorium, melatonin, or Valium.

9. The method according to claim 6 where the composition further comprises inactive ingredients where the composition and the inactive ingredients are in the form of an injection, ointment, cream, capsule or tablet.

10. The method according to claim 6 where the composition is in the form of a capsule or tablet.

11. The method according to claim 10 where 2 of the capsules or tablets are administered to the patient every 2-4 hours for 1-2 days followed by administering 1 of the capsules or tablets to the patient every 4-5 hours until symptoms do not reoccur after 2-4 hours following the administration.

12. A method for treating herpes simplex, herpes zoster, or both comprising administering to a patient in need thereof a tablet or capsule comprising:
 a) 10 mg Vitamin $B_2$;
 b) Vitamin $B_{co}$ which comprises 0.3 mg Vitamin $B_1$, 0.4 mg Vitamin $B_2$, 0.4 mg Vitamin $B_6$, 1.2 mcg Vitamin $B_{12}$, 60 mcg biotin, 4 mg niacin, 80 mcg folic acid, and 2 mg pantothenic acid;
 c) 40 mg concentrated Strobilanthes cusia;
 d) 100 mg Berberine;
 e) 200 mg concentrated Zizyphus semen;
 f) 150 mg L-lysine.

* * * * *